United States Patent [19]
Gyory

[11] Patent Number: 5,668,170
[45] Date of Patent: Sep. 16, 1997

[54] COMPOSITION AND METHOD ENHANCING TRANSDERMAL ELECTROTRANSPORT AGENT DELIVERY

[75] Inventor: J. Richard Gyory, San Jose, Calif.

[73] Assignee: ALZA Corporation, Palo Alto, Calif.

[21] Appl. No.: 612,378

[22] Filed: Mar. 7, 1996

Related U.S. Application Data

[63] Continuation of Ser. No. 274,619, Jul. 13, 1994, abandoned.

[51] Int. Cl.$^6$ .................................... A01N 43/02
[52] U.S. Cl. ................ 514/449; 114/48; 604/20; 424/78.1
[58] Field of Search ............... 514/449, 48; 604/20; 424/78.1

[56] References Cited

U.S. PATENT DOCUMENTS

| | | | |
|---|---|---|---|
| 4,153,689 | 5/1979 | Hirai et al. | 424/178 |
| 4,690,683 | 9/1987 | Chen et al. | 604/896 |
| 4,722,726 | 2/1988 | Sanderson et al. | 604/20 |
| 4,992,477 | 2/1991 | Geria et al. | 514/782 |
| 4,996,193 | 2/1991 | Hewitt et al. | 514/11 |
| 5,023,085 | 6/1991 | Francoeur et al. | 424/449 |

FOREIGN PATENT DOCUMENTS

| | | |
|---|---|---|
| 0552879 | 7/1993 | European Pat. Off. . |
| WO9116077 | 10/1991 | WIPO . |

OTHER PUBLICATIONS

Cosmetic Science and Technology, vol. 3, pp. 583–607, (1974), Balsam & Sagarin, Ed., Publisher, Interscience Publ.

Griffin, William C., Journal of the Society of Cosmetic Chemists, vol. V, No. 3, Nov., 1954, pp. 249–256, "Calculation of HLB Values of Non–Ionic Surfactants".

Srinivasan, V., et al., Journal of Pharmaceutical Sciences, vol. 79, No. 7, Jul. 1990, pp. 588–591, "Iontophoresis of Polypeptides: Effect of Ethanol Pretreatment of Human Skin".

Database WPI, Week 9408, Derwent Publication Ltd., London, GB; AN 94–061979 & JP, A, 06 016 538 (Japan Tobacco Inc.), 25 Jan. 1994, see abstract.

*Primary Examiner*—James J. Seidleck
*Assistant Examiner*—Dunc Truong
*Attorney, Agent, or Firm*—D. Byron Miller; Felissa H. Cagan; Steven F. Stone

[57] ABSTRACT

A composition comprises an agent to be delivered through a body surface and an electrotransport enhancer having a hydrophobic tail and a polar head of specific characteristics. An electrotransport delivery device is also provided having a reservoir comprising the agent to be delivered and the electrotransport enhancer of the invention. The electrotransport enhancers increase the electrotransport delivery rate of the agent through the surface while reducing the electrical resistance of the surface during electrotransport of the agent.

16 Claims, 1 Drawing Sheet

COMPOSITION AND METHOD ENHANCING TRANSDERMAL ELECTROTRANSPORT AGENT DELIVERY

RELATED APPLICATIONS

This application is a continuation, of application Ser. No. 08/274,619, filed Jul. 13, 1994, now abandoned and benefit of the filing date of said earlier filed application is claimed under 35 U.S.C. § 120.

TECHNICAL FIELD

This invention relates to the use of permeation enhancers for the electrotransport delivery of agents through a body surface. More particularly, this invention relates to permeation enhancers which reduce the electrical resistance of the surface and facilitate the electrotransport of agents, such as drugs, therethrough.

BACKGROUND ART

The delivery of drugs and drug precursors by diffusion through the skin offers improvements over more traditional delivery methods, such as subcutaneous injections and oral delivery. Transdermal drug delivery by passive diffusion avoids the hepatic first pass effect encountered with oral drug delivery. Passive transdermal drug delivery also reduces patient discomfort when compared to subcutaneous injection, and provides more uniform drug blood concentrations over time. The term "transdermal" delivery, broadly encompasses the delivery of an agent through a body surface, such as the skin, mucosa, or nails of an animal or the outer surface of a plant.

The skin functions as the primary barrier to the transdermal penetration of external substances into the body and represents the body's major resistance to the delivery of agents. Up to the present time, most efforts have been focussed on reducing the physical resistance or enhancing the permeability of the skin to the delivery of the therapeutic agent being delivered. Various methods for increasing the rate of transdermal drug diffusion have been used. For example, drug-impermeable backing layers made of metal, plastic and other materials have been employed in skin patches in order to limit diffusion of drugs away from the skin and, thereby, increase the diffusion of drugs into the skin. In addition, an increase in the rate of absorption of agents into the skin was produced by varying the temperature and the relative humidity of the atmosphere adjacent to the skin. Other efforts have been directed at abrading or piercing the skin by mechanically disrupting its outermost stratum corneum layer. Chemical absorption promoters or permeation enhancers have also been utilized, both as integral components of therapeutic compositions or applied prior to the therapeutic agent. These passive methods have generally proven ineffective in significantly increasing the amount of agent delivered, particularly in the case of hydrophilic drugs (eg, in the form of water soluble salts) and high molecular weight agents (eg, polypeptides and proteins).

"Electrotransport" involves the delivery of a agent through a body surface with the assistance of an electrical field. Electrotransport, thus, refers generally to the passage of an agent through a substrate, such as the skin, mucous membranes, or nails, which is at least partially induced by circulating an electrical current through the substrate. Many agents, including therapeutic drugs and precursors thereof, may be introduced into the human body by electrotransport. The electrotransport of an agent through a body surface may be attained by various methods. One widely used electrotransport method is iontophoresis, which involves the electrically induced transport of charged ions. Electroosmosis, another type of electrotransport, involves the movement of a liquid out of, or through, a biological membrane under the influence of an electrical field. Electroporation, still another type of electrotransport, involves the movement of an agent through transiently-created pores formed in a biological membrane under the influence of an electric field. When any given agent is electrotransported, more than one of these methods may occur simultaneously to some extent. The term electrotransport, as used herein, is given its broadest possible interpretation to include the electrically induced or enhanced transport of charged and uncharged agents or mixtures thereof, regardless of the specific mechanism(s) by which the agent(s) is(are) actually transported.

Electrotransport devices typically require at least two electrodes, both being in electrical contact with some portion of the skin, nails, mucous membrane, or other membrane surfaces of the body. One electrode, commonly referred to as the "donor" or "active" electrode, is the electrode from which an agent, such as a drug or drug precursor, is delivered into the body. The other electrode, typically termed the "counter" or "return" electrode, serves to close the electrical circuit through the body. For example, if the ionic agent to be delivered is a cation, i.e. a positively charged ion, the anode will be the active or donor electrode while the cathode completes the circuit. Alternatively, if the agent is an anion, ie, a negatively charged ion, the cathode will be the donor electrode while the anode completes the circuit. When anionic and cationic drugs need to be delivered at the same time, both the anode and cathode may be used for this purpose and the anionic drug placed in the cathode while the cationic drug is placed in the anode. In addition, electrotransport delivery devices typically include an electrical power source in the form of one or more batteries, and an electrical control mechanism designed to regulate the flow of electric current through the electrodes and thereby the rate of drug delivery. Alternatively, the power may be supplied, at least in part, by a galvanic couple formed by contacting two electrodes made of dissimilar materials. A complete electrical circuit is formed by electrically contacting one pole of the power source to the donor electrode, the donor electrode to the body, the body to the counter electrode, and the counter electrode to the opposite pole of the power source. The donor electrode typically includes a reservoir or source of the agent or drug to be delivered. The donor reservoir may take the form of a pouch, a cavity, a porous sponge, a pad, and a pre-formed gel body, among others. The counter electrolyte likewise typically includes a reservoir containing a biocompatible electrolyte. Such reservoirs are electrically connected to the anode or cathode of the electrotransport device to provide either a fixed or a renewable source of one or more electrolytes, therapeutic agents or drugs.

It is known that electrotransport drug flux is roughly proportional to the level of electric current applied by the device. However, there is a limit to the amount of current which may be comfortably tolerated by a patient. This problem becomes more acute as the size of the electrotransport system and, therefore, the skin contact areas of the electrodes is reduced, as is the case in portable/wearable systems. As the skin contact area of an electrotransport device decreases, the current density, (ie, the amount of current per unit of skin contact area) applied by the device increases. Thus, there is a limit to the level of electric current which may be applied by any electrotransport device of a given size and, this current limit becomes lower as the size (ie, the skin contact area) of the device is reduced. In certain instances, electrotransport devices operating at these current limits have been unable to deliver sufficient amounts of drug to effectively treat a disease. In those cases, the incorporation of a permeation enhancer into the electrotransport device may increase the amount of the drug delivered, and help maintain a higher and therapeutically effective concentration of drug in the blood. In the context of this application, the terms "permeation enhancer" include absorption promoters and surfactants and broadly describe a chemical species which either reduces the physical resistance of a body surface to the passage of an agent therethrough or, as electrotransport enhancers do, alters the ionic selectivity of the body surface, increases the electrical conductivity or the permeability of the body surface, and/or the number of agent-transmitting pathways therethrough. The use of electrotransport enhancers may also help reduce the size of the electrotransport device by requiring a reduced total electric current and thereby a reduced electrode skin-contact area for achieving a particular current density. A reduction in the size of the device will also, most likely, improve patient comfort and reduce manufacturing costs.

A limited number of electrotransport enhancers for the delivery of agents have been disclosed in the literature. Ethanol, for instance, has been utilized as an electrotransport enhancer for polypeptides by Srinivasan et al., (Srinivasan et al, "Iontophoresis of Polypeptides: Effect of Ethanol Pretreatment of Human Skin", J Pharm Sci 79(7):588–91 (1990)). In U.S. Pat. No. 4,722,726 to Sanderson et al., the skin surface is pretreated with a surface active agent prior to the application of the drug to the skin to reduce competition with tissue ions migrating outwardly through the skin, with sodium lauryl sulfate being a preferred surface active agent. U.S. Pat. No. 5,023,085 to Francoeur et al. discloses the use of unsaturated $C_{14}$–$C_{20}$ acids, alcohols, amines, and esters, along with ketones for the iontophoretic delivery of certain drugs. Laid Open Patent Application WO91/16077 discloses the use of fatty acids, such as oleic acid, lauric acid, capric acid, and caprylic acid, as penetration enhancers for the iontophoretic delivery of drugs.

Thus, there is a continuing need to provide transdermal electrotransport enhancers that provide increased rates of delivery of agents, such as drugs or precursors thereof, in the absence of detrimental effects, such as excessive electric current, to the patient.

DISCLOSURE OF THE INVENTION

This invention relates to a composition for electrotransport agent delivery, an electrotransport device containing the composition, and a method of delivering an agent by electrotransport which utilizes the composition. The composition comprises at least one agent to be transdermally delivered through a body surface and at least one electrotransport enhancer of its delivery. The transdermal electrotransport enhancer utilized herein comprises a hydrophobic tail and a polar head, and has a hydrophile-lipophile balance (HLB) number greater than about 6, the polar head having a molecular weight (MW) of less than 150 Daltons and being either neutral or ionizable when placed in aqueous solution.

This invention also relates to a transdermal electrotransport delivery device that comprises a donor reservoir containing the agent(s) to be delivered through a body surface and the electrotransport enhancer(s) of this invention.

The electrotransport enhancer of this invention may be utilized to improve the rate of electrotransport delivery of an agent through a body surface by applying to the body surface a composition comprising the enhancer and the agent, and applying an electrical current through the surface to induce the electrotransport delivery of the agent therethrough, and reducing the surface's electrical resistance and increasing the flux of the agent therethrough when compared with the flux obtained in the absence of enhancer.

MODES FOR CARRYING OUT THE INVENTION

This invention improves on prior art technology suitable for the delivery of agents, such as drugs and the like, through a body surface, in order to make available sufficiently high blood levels of the agents, eg, to treat previously untreatable diseases, in the substantial absence of detrimental effects to the patient. The rate at which an agent, such as a drug or drug precursor, is delivered to the body may be improved by modifying the design of the delivery device and/or the contents of the delivery composition. One way of increasing the rate of delivery of an agent by electrotransport, is to reduce the electrical resistance of the body surface (eg, skin). This, in turn, reduces the power requirements of the system and permits a reduction in the size of the device. In the present invention, the delivery of the agent (eg, drug) in conjunction with the electrotransport enhancer of the invention increases the electrotransport flux of the agent through the body surface and/or decreases the electrical potential (voltage) required to electrotransport the agent through the body surface.

Thus, the electrotransport enhancer utilized in the present invention increases the electrotransport flux of the agent through the surface and/or decreases the electrical resistance of the body surface and, thereby, reduces the voltage across the surface at a select current level by altering the ionic selectivity of the body surface, increasing its electrical conductivity or its permeability to the agent, and/or increasing the number of pathways available within the surface for the passage of the agent therethrough. Increased flux of various agents and/or reduced voltage was obtained with enhancer molecules having a lipophilic tail and polar head group of less than about 150 Dalton molecular weight (MW) and preferably in the range of about 16 to 150 Dalton MW. When the polar head group becomes larger, the potentiating effect on the transdermal electrotransport of the agent by the enhancer tends to diminish. This may be caused by the large polar head groups physically impeding the penetration of the enhancer into the body surface. On the other hand, within the specified size, the polar head groups may provide the electrotransport enhancer with increased aqueous solubility and help create a more hydrophilic pathway for the agent through the body surface. In some instances, the polar head group may also interact with the agent to be delivered to increase the solubility of the latter. A "polar head group", as used herein, is a chemical residue, having a positive or negative charge, located at one end of the enhancer molecule, eg, at the end of a straight chain comprising saturated aliphatic residues. Examples of polar head groups for use in the present electrotransport enhancers include alcohols (—OH), amines (—$NH_2$), mono- and di-substituted amines (—$NR_2$), quaternary ammonium salts (—$N^+R_4$), sulfates (—$SO_4^{-2}$), sulfoxides (=SO), esters (—$COO^-R^+$), amides (—$CONH_2$), mono- and di-substituted amides (—$CONR_2$), wherein R is selected from aliphatic, allcyclic and aromatic residues which may be substituted with N, O, S, or halogen, and alkali metal salts thereof such as sodium or potassium salts, among others.

In addition to the above characteristics relating to the polar head group, the electrotransport enhancers of the invention were selected by their hydrophile-lipophile balance (HLB) characteristics. The HLB is an empirical value which was introduced by W. C. Griffin in 1949 and broadly reflects the balance of size and strength of the hydrophilic and lipophilic groups present in a molecule. Molecules that are highly lipophilic have low HLB values, ie, below about 5.0, and highly hydrophilic molecules have HLB values, above about 11.0. Those with intermediate characteristics, accordingly, have intermediate HLB values. An HLB number greater than about 7 indicates that the molecule is more hydrophilic than lipophilic. The chemical compounds providing the highest increases in agent flux and/or decreases in cell voltage are those having an HLB number greater than about 6, and at times even greater than about 15, and as high as about 40. The HLB number, thus, reflects a measure of the hydrophile-lipophile balance of the enhancer and is a relative proportion of its hydrophilic to hydrophobic character. Most surfactants have HLB numbers in the range of 0 to 20, although HLB values of up to 40, and higher are also possible. Thus, most of the electrotransport enhancers utilized herein either possess a rather balanced hydrophilic and lipophilic character or are more hydrophilic than lipophilic as their HLB numbers increase. HLB numbers for a variety of hydrophilic-lipophilic molecules have been calculated and are in the published literature. A thorough discussion of HLB values and non-ionic surfactant HLB numbers is provided for instance by Griffin, W. C., "Calculation of HLB Values of Non-ionic Surfactants", J. Soc. Cos. Met. Chem. 5:249–256 (1954); and Griffin, W.C., in Cosmetic Science and Technology, Vol. 3, Ch. XLIV, Balsam and Saparin, Eds., pp. 583–607 (1974), the pertinent portions of which are incorporated herein by reference.

The transdermal electrotransport enhancer suitable for use herein may be charged or uncharged. If the enhancer is charged, the electrotransport enhancer preferably has a charge opposite that of the agent. Enhancers which are uncharged or have a charge opposite the charge of the agent to be delivered are preferred for at least two reasons. First, an enhancer having a charge opposite that of the agent being delivered does not compete with the agent for carrying the electric current, which competition results in lower agent flux per unit of applied current. Second, once an enhancer having the same charge as that of the agent is delivered into the skin, the skin becomes charged and, therefore, in most instances, less permeable to ions (eg, agent ions) having the same charge as the enhancer.

In a still more preferred embodiment, the transdermal electrotransport enhancer has a hydrophobic tail which comprises a $C_{10}$–$C_{12}$ saturated aliphatic residue, and more preferably a linear one. This group of electrotransport enhancers encompasses saturated aliphatic alcohols, amines, mono- and di-substituted free amines, quaternary ammonium salts, sulfates, acid esters, di-sulfoxides, sulfoxides, free amides, mono- and di-substituted amides, and salts thereof. The compositions of this invention may include one or more of these enhancers as well as mixtures thereof, and mixtures thereof with other enhancers such as unsaturated derivatives thereof, organic acids, $C_8$–$C_{20}$ unsaturated aliphatic acids, $C_8$–$C_9$ and $C_{13}$–$C_{20}$ saturated analogues thereof, and esters thereof, and the like. Examples of electrotransport enhancers in accordance with the present invention include lauryl amine, sodium laurate, decyl methyl sulfoxide, dodecyl pyrrolidone, dimethyl lauramide, N,N-dimethyl-1-dodecaneamine (dimethyl lauramine) and salts thereof N,N-didodecyl-1-dodecaneamine (trilaurylamine), and sodium lauryl sulfate, mixtures thereof, and mixtures thereof with aliphatic acids such as lauric acid, among others.

In another embodiment, the electrotransport enhancer is uncharged or neutral in aqueous solution. A "neutral electrotransport enhancer", as used herein, is an enhancer having less than about 5% by weight ionization in aqueous solution. Neutral electrotransport enhancers are particularly suitable when the agent to be delivered is charged in aqueous solution but no suitable enhancer which is oppositely charged in solution can be found. Neutral electrotransport enhancers are significantly better enhancers of agent flux through a body surface than same-charged molecules when they are present in the composition along with the ionizable agent. For example, in tests conducted with the anti-asthmatic agent sodium cromolyn, dodecyl pyrrolidone increases anionic cromolyn flux by more than 50% and lowers skin resistivity to the drug by more than 30%. Another example of the suitability of the neutral electrotransport enhancers is provided by the increase in both flux and conductivity observed when dimethyl lauramide is added to ketoprofen, a univalent anionic anti-inflammatory agent. The group of neutral electrotransport enhancers suitable for use with this invention encompasses linear dialiphatic or aliphatic, sulfoxides, pyrrolidones, esters, alcohols, unsubstituted or mono- or di-substituted amides, and some di-substituted amines, among others. Specific neutral electrotransport enhancers include $C_1$–$C_{10}$ aliphatic esters of saturated $C_{10}$–$C_{12}$ aliphatic acids. Examples of electrotransport enhancers displaying a neutral or non-ionized character in aqueous solution include n-decyl methyl sulfoxide, dodecyl pyrrolidone, dimethyl lauramide, and mixtures thereof. Neutral electrotransport enhancers are preferred in order to avoid transport competition between similarly charged ionized permeation enhancers and agents to be delivered.

The composition and electrotransport delivery device of this invention are useful in the delivery of a broad class drugs that is deliverable through body surfaces and membranes, including skin, mucosa and nails. As used herein, the expressions "agent", "drug" or "drug precursor" are used interchangeably, and are intended to have their broadest interpretation as any therapeutically active substance which is delivered to a living organism to produce a desired, usually therapeutic, effect. This class of drugs includes therapeutic agents in all of the major therapeutic areas including, but not limited to, anti-infectives such as antibiotics and antiviral agents; analgesics such as fentanyl, sufentanil, and buprenorphine, and analgesic combinations; anesthetics; anorexics; antiarthritics arthritics; antiasthmatic agents such as terbutaline; anticonvulsants; antidepressants; antidiabetics agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetics; xanthine derivatives; cardiovascular preparations including calcium channel blockers such as nifedipine; beta-agonists such as dobutamine and ritodrine;

beta blockers; antiarrythmics; antihypertensives such as atenolol; ACE inhibitors such as ranitidine; diuretics; vasodilators including general, coronary, peripheral and cerebral; central nervous system stimulants; cough and cold preparations; decongestants; diagnostics; hormones such as parathyroid hormones; hypnotics; immunosuppressives; muscle relaxants; parasympatholytics; parasympathomimetics; prostaglandins; proteins; peptides; psychostimulants; sedatives and tranquilizers.

More specifically, the composition and electrotransport delivery device of this invention are useful in the controlled delivery of drugs such as baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil, among others. The invention is particularly useful in the controlled delivery of peptides, polypeptides, proteins, or other macromolecules difficult to deliver transdermally or transmucosally because of their size. These macromolecular substances typically have a molecular weight of at least about 300 Daltons, and more typically, a molecular weight in the range of about 300 to 40,000 Daltons. Examples of peptides and proteins which may be delivered using the composition, method and device of the present invention include, without limitation, LHRH, LHRH analogs such as buserelin, gonadorelin, naphrelin and leuprolide, GHRH, GHRF, insulin, insulinotropin, heparin, calcitonin, octreotide, endorphin, TRH, NT-36 (N-[[(s)-4-oxo-2-azetidinyl]carbonyl]-L-histidyl-L-prolinamide), liprecin, pituitary hormones (e.g., HGH, HMG, HCG, desmopressin acetate), follicle luteolds, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSFs, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta. The electrotransport composition of the present invention may also comprise other chemical additives which further increase body surface conductivity or permeability. Suitable additives include buffers, solvents such as ethanol, propyleneglycol, glycerol, and water, which may increase drug or enhancer solubility and/or increase charged ion concentrations, while others, such as fatty acids may, in addition increase agent flux. Examples of fatty acids suitable for use herein are oleic acid, lauric acid, capric acid, caprylic acid, and the like, among others. Other additives used in compositions suitable for transdermal electrotransport of drugs may also be present in the composition.

These electrotransport enhancers must be pharmaceutically acceptable and biocompatible since they are utilized in the transdermal delivery of a drug or agent through a body surface. The term "biocompatible", as used herein, means that the enhancer does not produce significant detrimental side effects, such as irritation or sensitization, when contacted with the chosen body surface.

The composition of the invention typically comprises an amount of the agent, such as a drug or a drug precursor, that upon transdermal electrotransport delivery will provide a therapeutic amount of the agent and maintain this level for a period of time. These amounts will vary with the specific agent to be delivered. The ingredients in the composition are typically added and mechanically mixed and incorporated into the donor reservoir of an electrotransport delivery device prior to its use. The amount of electrotransport enhancer required for addition to the donor reservoir of an iontophoretic delivery device depends upon a multitude of factors. For example, the properties of the chosen agent and enhancer, the applied voltage, and the desired delivery rate are a few of the variables to be taken into account to determine the electrotransport enhancer concentration. Generally, the electrotransport enhancers of the present invention are present in the composition in an amount of about 0.01 to 20 wt % based on the weight of the agent-enhancer solution, more preferably about 0.1 to 15 wt % of the agent-enhancer solution, and still more preferably up to about 5 wt % of the agent-enhancer solution. The composition of the invention is typically provided to the patient in a donor reservoir of a transdermal electrotransport device. Typical electrotransport devices are comprised of an independent electrical power source (eg, one or more batteries), a donor or active electrode and a counter electrode, and an electrical control mechanism designed to regulate the level of applied electric current and, thereby, the rate of drug delivery.

Figure 1:
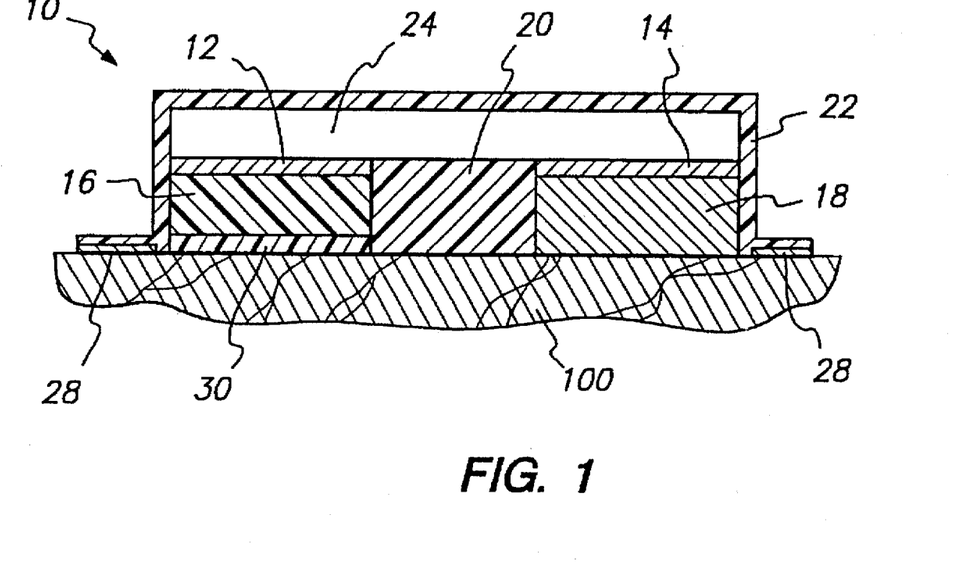
FIG. 1 is a sectional view of one example of an electrotransport device which may be used to deliver the composition of the present invention.

One embodiment of an electrotransport delivery device of the present invention is illustrated in FIG. 1. The device 10 has two current conducting members, referred to herein as a donor electrode 12 and a counter electrode 14. The donor and counter electrodes 12 and 14 are positioned adjacent to the donor reservoir 16 and the optional counter reservoir 18, respectively. The donor reservoir 16 contains the agent to be delivered, while the optional counter reservoir 18 contains a biocompatible electrolytic salt. The donor electrode 12 and donor reservoir 16 are separated from the counter electrode 18 and optional counter reservoir 18 by an electrical insulator 20. The device 10 also has a backing layer 22 composed of a water-proof, and preferably electrically insulating material. Electric power is supplied by the power source, shown schematically as layer 24 in FIG. 1, which may be a battery or a series of batteries. The power source may optionally include current controlling circuitry. Power source 24 is in electrical contact with electrodes 12 and 14, such that each electrode is in contact with the opposite pole of the power source 24. The device adheres to the body surface 100 by means of a peripheral adhesive layer 28. An optional passive flux control membrane 30 may be positioned between the donor reservoir 16 and the body surface 100 for controlling passive agent delivery (ie, flux occurring in the absence of any applied electrical potential). The device 10 of FIG. 1 is merely one example of a suitable electrotransport delivery device to practice the present invention. In addition, the device may contain other features, such as a removable protective liner (not shown) on the skin-contacting face of the device. Furthermore, certain components in device 10 are optional according to the present invention, such as the counter reservoir 18 and the independent power source 24, if the electrodes 12 and 14 are chosen such that they form a galvanic couple.

The electrotransport enhancing composition of this invention can also be used in electrotransport devices having a table-top electrical controller and electrodes connected to the controller through long (eg, 1 to 3 m) electrical cables. These "remote" electrodes may be attached to separate body surface locations while the patient remains immobile (eg, sitting or lying) near the controller. There are numerous electrotransport device configurations known in the art, all of which are contemplated for use with the electrotransport enhancing composition of the invention. Thus, device 10 of FIG. 1 is presented solely for illustrative purposes and represents only one example of a device which may be used with the composition and method of the present invention.

The electrodes 12 and 14 may be composed of an electrically conductive material such as a metal. For example, the electrodes 12 and 14 may be formed from metal foil, metal screen, metal deposited or painted on a suitable backing, such as by calendaring or film evaporation, or by embedding a metal powder in a binder matrix. Examples of suitable metals include silver, zinc, silver chloride, aluminum, platinum, stainless steel, gold, and titanium. In one preferred embodiment the anodic electrode is comprised of silver while the cathodic electrode is comprised of silver chloride. Silver is preferred, as an anode, over other metals because silver ions, produced by the oxidation of the silver anode ($Ag \rightarrow Ag^+ + e^-$), have relatively low toxicity to humans. Silver chloride is preferred as a cathode because the reduction of silver chloride produces chloride ions ($AgCl + e^- \rightarrow Ag + Cl^-$) which are endogenous to the human body. Alternatively, the electrodes 12 and 14 may be formed of a polymer matrix containing a conductive filler such as a metal powder, powdered graphite, carbon fibers, or other electrically conductive filler material. The polymer-based electrodes may be produced by mixing the conductive filler in a polymer matrix.

The electrotransport delivery device of this invention can be powered in various forms. If the donor and counter electrodes are of dissimilar metals or have different half cell reactions, the device may generate its own electrical power. Typical materials which provide a galvanic couple include a zinc anodic electrode and a silver chloride cathodic electrode. Such a galvanic couple powered system, absent some controlling means, activates automatically when body tissues and/or fluids complete the electrical circuit with the device. Numerous other galvanic couple systems potentially useful in the present invention are known in the art and need not be further described herein. (See for example, CRC Handbook of Chemistry and Physics, pp D133–D138, $62^{nd}$ edition (1981–1982), the relevant portion of which is incorporated herein by reference for the disclosures of electrochemical half cell reactions which may be combined to form a galvanic couple). In most cases, however, a separate electrical power source 24, such as the one shown in FIG. 2, will be required to power the electrotransport device. The power source 24 may include one or more batteries, connected in series or in parallel, and positioned between the counter electrode 14 and donor electrode 12, such that the donor electrode 12 is connected to one pole of the power source 24 and the counter electrode 14 is connected to the opposite pole. One or more 3 V button cell batteries, eg, PANASONIC® Model CR 2025, are suitable to power electrotransport devices. Power source 24 may also include electronic circuitry for controlling the applied electric current (eg, current level, pulsed or DC, frequency, duty cycle, etc.) as well as the operation of the electrotransport device, such that the patient may manually turn the system on and off, as in a device suitable for an on-demand medication regime, or to automatically turn the system on and off with some desired periodicity, for example, to match the natural or circadian patterns of the body. A relatively simple controller or microprocessor may be provided as well to control the current as a function of time or to generate complex current wave forms such as pulses or sinusoidal waves. The control circuitry may also include a biosensor and a feedback system to monitor biosignals, provide an assessment of the progress of the therapy, and adjust the delivery of the drug accordingly.

The donor reservoir 16 and the optional counter reservoir 18 may be formed of any material adapted to hold a sufficient quantity of liquid therein in order to permit the transport of the agent therethrough by electrotransport. For example, gauzes, pads or sponges composed of cotton or other absorbent fabric, both natural and synthetic, may be used. More preferably, the matrices of the reservoirs 16 and 18 are composed, at least in part, of a hydrophilic polymer material. Hydrophilic polymers are typically preferred because water is a preferred biocompatible solvent suitable for solubilizing many drugs, and hydrophilic polymers have a relatively high equilibrium water content. More preferably, the matrices of the reservoirs 16 and 18 are solid polymer matrices composed, at least in part, of an insoluble hydrophilic polymer. Insoluble hydrophilic polymer matrices are preferred for structural reasons over soluble hydrophilic polymers. The matrices may be cross-linked with the agent in place such as in the case of a silastic matrix, or the polymers may be prefabricated and sorbed with the components from solution as is the case with cellulose, woven fiber pads and sponges.

The agent reservoirs 16 and 18 may alternately be made of a hydrophilic polymeric gel which is swellable or soluble in water. The polymers may be blended with the drug in any ratio, the dry weight drug loading being preferably a few percent up to about 50 wt % of the reservoir. The polymers may be linear or cross-linked. Suitable hydrophilic polymers include co-polyesters such as HYTREL® (DuPont De Nemours & Co., Wilmington, Del.), polyvinyl pyrrolidones, polyvinyl alcohol, polyethylene oxides such as POLYOX® (Union Carbide Corp.), CARBOPOL® (BF Goodrich of Akron, Ohio), blends of polyoxy ethylene or polyethylene glycol with polyacrylic acid such as POLYOX® blended with CARBOPOL®, polyacrylamide, KLUCEL®, cross-linked dextran such as SEPHADEX® (Pharmacia Fine Chemicals, AB, Uppsala, Sweden), WATER LOCK® (Grain Processing Corp., Muscatine, Iowa) which is a starch-graft-poly(sodium acrylate-co-acrylamide) polymer, cellulose derivatives such as hydroxyethyl cellulose, hydroxypropyl methylcellulose, low-substituted hydroxypropyl cellulose, and cross-linked Na-carboxymethyl cellulose such as Ac-Di-Sol® (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred. This list is merely exemplary of the materials suited for use in this invention. Other suitable hydrophilic polymers have been listed by Scott and Roff in (Scott, J. R., & Roff, W. J., in Handbook of Common Polymers, CRC Press (1971), the relevant portion of which is incorporated herein by reference.

The matrices of the reservoirs 16 and 18 may optionally contain a hydrophobic polymer for enhanced structural rigidity. The hydrophobic polymer is preferably heat fusible, in order to improve the lamination of the reservoirs 16 and 18 to adjacent components, such as the insulator 20 shown in FIG. 1. Suitable hydrophobic polymers for use in the reservoir matrices include, but are not limited to, polyisobutylenes, polyethylene, polypropylene, polyisoprenes and polyalkenes, rubbers, polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched $C_{10}$–$C_{24}$ alkyl maleamic acids, glycol diacrylates, and blends thereof. Most of the above-mentioned hydrophobic polymers are heat fusible. Of these, polyisobutylenes are preferred.

The reservoir matrices may be a polymeric matrix structure formed by blending the desired agent, drug, electrolyte, or other component(s), with the polymer by such processes as melt blending, solvent casting, or extrusion. Typically, the donor reservoir 16 contains a drug to be delivered, while the counter reservoir 18 contains an electrolyte, eg, a water soluble biocompatible salt. In addition to the drug and electrolyte, the reservoirs 16 and 18 may also contain other conventional materials such as dyes, pigments, inert fillers, and the like. The counter reservoir 18 may contain one or more biocompatible electrolytic salts, such as sodium chloride. The insulator 20 prevents direct ion transport, ie, short circuiting, between the donor reservoir 16 or the donor electrode 12 and the counter electrode 14 or optional counter reservoir 18. Insulator 20 is made of material that is impermeable to the passage of water, ions, and electrons. Preferably, the insulating material is a material capable of strong bonding with the reservoir polymers, thereby providing further overall structural integrity for the device. Preferred insulating materials include poly(isobutylenes) and ethylene vinyl acetates (EVA). Similarly, the backing layer 22 is composed of a material which is water-proof and preferably electrically insulating. The primary function is to prevent electrical short-circuiting. In addition, the backing layer 22 may provide some structural integrity to the device.

The composition of the invention is intended for transsurface administration, and preferably transdermal administration. The amount of agent to be delivered need not be specified herein, and will depend on the agent itself and the medical condition being treated.

Having thus generally described the invention, the following examples will illustrate how variations of the above-described parameters provide therapeutically effective electrotransport systems.

EXAMPLES

Preparation of Skin Strips

Human cadaver skin strips were prepared by removing about 1 mm thick samples with an electric dermatome. These skin strips were then placed in polyethylene bags, which were sealed and temporarily stored at about 4° C.

Preparation of Skin Disks

Prior to their use in the electrotransport cell, the skin strips were placed for about 90 seconds in one-liter beakers containing water at 60° C., and gently stirred. The skin strips were then removed and placed onto the absorbent side of a piece of BENCHKOTE material with the dermis side down. The epidermis was removed from each strip with a round-tip spatula while the dermis was retained with the aid of flat tipped tweezers. Each epidermis, stratum corneum side up, was transferred to a 2" deep Pyrex glass tray containing water. Each floating epidermis was stretched essentially flat. After removing each epidermis from the water, 2.22 cm (7/8 in.) diameter disks were punched out of areas of each epidermis having negligible surface damage. The punched disks were stored with water droplets at 4° C. in a sealed container to maintain moisture and subsequently mounted between the donor reservoir 44 and counter reservoir 46, as shown in FIG. 2, with the stratum corneum side facing the donor compartment.

Preparation of Electrotransport Delivery Device and Composition

Figure 2:
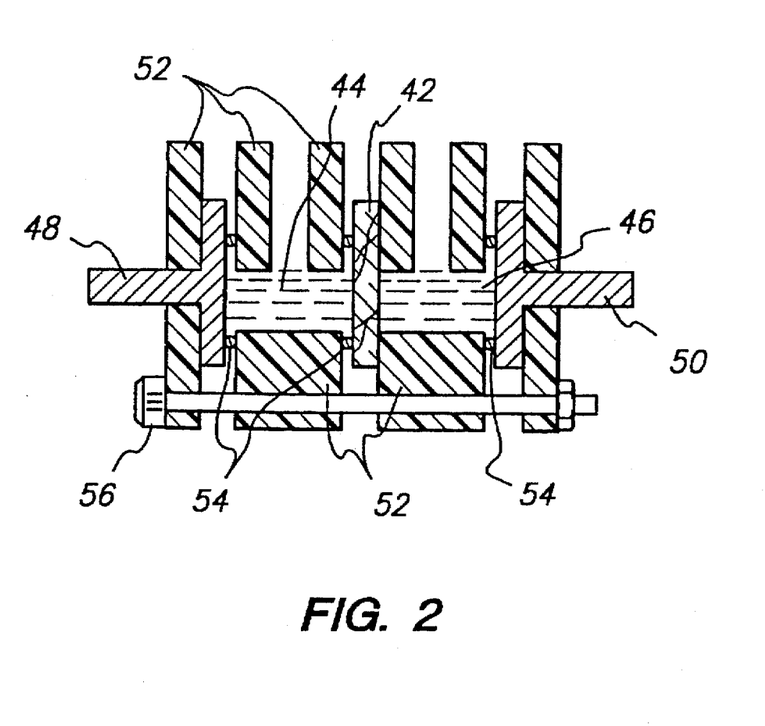
FIG. 2 is a sectional view of a two compartment cell used for in vitro testing of transdermal electrotransport drug flux.

Human cadaver epidermis disks 42 were mounted in a 2-compartment polycarbonate electrotransport permeation cell illustrated in FIG. 2. The cell was comprised of a polycarbonate support structure 52, having rubber O-ring seals 54, held together with stainless steel bolt and nut 56. The human epidermis disks 42 were mounted between the anodic compartment 44 and the cathodic compartment 46. A silver anode 48 was placed adjacent the anodic compartment 44 and a silver chloride cathode 50 was placed adjacent the cathodic compartment 46. The area of the human epidermis 42 exposed for transport was about 1.26 $cm^2$ and the volume of each of compartments 44 and 46 was about 2 ml. The electrodes 48, 50 were electrically connected to a galvanostat (not shown in FIG. 2), which can be set to apply the voltage needed to achieve a constant predetermined level of electric current, ie, 126 μA.

Solutions of the drug to be transported through the skin disks 42, and each of the electrotransport enhancers to be tested were placed at different times in the anodic donor compartment 44. Dulbecco's phosphate buffered saline (approximately 0.1 5N NaCl, with minor amounts of other ions, pH 7.0) was placed in the cathodic receptor compartment 46. The skin resistance was calculated from the voltages applied by the galvanostat according to Ohm's law:

$$R_{skin} = V/I,$$

where V is the potential applied by the galvanostat and I is the electric current, 126 microamps. The drug flux was determined by periodic sampling of the solution in the receptor compartment 46.

Example 1

Enhancement of Electrotransport Delivery of Metoclopramide HCl

Aqueous metoclopramide HCl (an anti-emetic drug salt) solutions having a concentration of about 100 mg/ml were placed in the donor compartment. The pH in the donor compartment was not adjusted but remained naturally at about 5.0 to 5.5 throughout the experiments. In an aqueous solution, metoclopramide HCl forms a positively charged drug ion and the electrotransport enhancers utilized in this experiment were representative of the following different categories of surfactants:

(a) Anionic molecules, eg, sodium lauryl sulfate;

(b) Weak polar molecules, eg, polyethylene glycol monolaurate (ie, PEG-4 monolaurate), polyethylene glycol di-laurate (ie, PEG-4 di-laurate), polyoxyethylene(23)

lauryl ether (Brij 35 sold by Signma Chemical Co., St. Louis, Mo.), and lauryl lactate;

(c) Hydrophilic molecules containing sugars, eg, sucrose laurate, sorbitan monolaurate, and polysorbate-20;

(d) Hydrophilic molecules containing nitrogen, eg, dimethyl lauramide, dodecyl pyrrolidone, urea, laurylamine, and dimethyl dodecylamine oxide;

(e) Miscellaneous group, eg, decyl methyl sulfoxide, and amphoteric molecules, such as lauramphocarboxy propionate.

Each surfactant was added to a final concentration of 10 mM (except for dodecylpyrrolidone which was added to a final concentration of 100 mM) to the donor solutions for comparative purposes. The system was maintained at about 32° C. by means of a HAAKE Model D1 heating block/water bath. A constant electric current of 126 µA, ie, 100 µA/cm$^2$, was applied with the galvanostat across the anode 48 and cathode 50 throughout the entire procedure, and the cell voltage was monitored over the entire time and then averaged.

Samples were automatically taken from the receptor compartment every one to two hours, except for overnight periods, with an autosampler (ISCO Model 2230 Lincoln City, Nebr.) and a metering pump. The metoclopramide concentration in the receptor compartment was determined by light absorption at 310 nm wavelength, using a standard curve of concentration v. absorption. The absorption measurements were obtained with a 8452A UV/vis spectrophotometer (Hewlett-Packard, Palo Alto, Calif.). Three cells were typically used for testing each of the electrotransport enhancer compositions to minimize error, and tissue from the same donor was used in the three cells, two of the cells having the selected electrotransport enhancer in the donor compartment, and the third cell being a control cell which contained no electrotransport enhancer.

Generally, the flux and voltage measurements were taken at or after about 5 hours, at which time these levels achieved a steady state.

The normalized mass flux and voltage values obtained in the presence of each one of the electrotransport enhancers for the steady state flux of metoclopramide are shown in Table 1. That is each value obtained in the presence of an enhancer is divided by the control value. Thus, the control value for the normalized flux and cell voltage are both 1, and the normalized values in the presence of an enhancer deviate from this value as they influence the resistivity of the skin and/or metoclopramide flux through the skin. For instance, a metoclopromide flux value of 1.87 indicates an almost doubling of the amount of the drug delivered when dimethyl lauramide was added to the donor composition. Similarly, a cell voltage value of 0.45 indicates a cell voltage and, therefore, skin resistance of about one-half that of the control, when dimethyl lauramide is added to the donor composition.

TABLE 1

Normalized Mass Flux and Cell Voltage for Various Electrotransport Enhancers

| Permeation Enhancer | HLB* No. | Polar Head (Daltons) | n** | Normalized Metoclopramide Mass Flux (after 5 hrs) | Normalized Cell Voltage (after 5 hrs) |
|---|---|---|---|---|---|
| Control (no enhancer) | N/A | N/A | 3 & 4 | 1.00 | 1.00 |
| Lauryl amine | 11 | 17 | 2 | 0.136 | .22 |
| n-Decyl methyl sulfoxide | 32 | 63 | 3 | 1.59 | .44 |
| Dodecyl pyrrolidone | 8 | 72 | 3 | 1.68 | .35 |
| Dimethyl lauramide | 8 | 72 | 3 | 1.87 | .45 |
| Sodium lauryl sulfate | 40 | 96 | 3 | 1.64 | .76 |
| Sorbitan monolaurate | 8.6 | 191 | 3 | 1.01 | .98 |
| PEG-4 monolaurate | 9.5 | 221 | 2 | 1.05 | .74 |
| Laurampho-carboxy-propionate | 54 | 260 | 2 | 0.99 | .93 |
| BRIJ 35 | 17 | 1029 | 2 | 1.04 | .94 |
| Polysorbate-20 | 17 | 2783 | 2 | 0.92 | .96 |
| Lauryl lactate | 4.7 | 89 | 3 | 0.97 | .92 |
| PEG-4 Dilaurate | 6 | 248 | 2 | 0.97 | .76 |

*HLB denotes hydrophile-lipophile balance.
**n denotes number of samples tested.

As can be seen from Table 1, electrotransport enhancers having polar head groups of less than about 150 Daltons and HLB values greater than about 6 evidenced drug flux increases greater than 50% above control. Amongst the permeation enhancers tested, the ones showing superior characteristics include n-decyl methyl sulfoxide, dodecyl pyrrolidone, dimethyl lauramide, and sodium lauryl sulfate. Some of these are anionic surfactants, such as sodium lauryl sulfate which enhanced mass flux and decreased skin resistance. Enhancers with weakly polar groups, such as PEG-4 monolaurate, PEG-4 dilaurate, Brij 35, and lauryl lactate, reduced skin resistivity, none of these enhanced the mass flux of metaclopramide. Sorbitan monolaurate, and polysorbate-20 have hydrophilic sugar moieties but fail to have a significant effect on either the electrotransport flux of metaclopramide or the skin resistivity. Dimethyl lauramide, dodecylpyrrolidone, urea, laurylamine, and dimethyl dodecylamine oxide all contain nitrogen in their hydrophilic heads. Both dimethyl lauramide and dodecylpyrrolidone were very effective enhancers. Laurylamine, a positively charged molecule, not only did not enhance, but significantly decreased the flux of the cationic metoclopramide (ie, due to competition between laurylamine and metoclopromide and due to charging of the skin). Decyl methyl sulfoxide acted as a good enhancer, whereas the sole amphoteric compound, lauramphocarboxy propionate, which has a polar head that is too large, did not appear to affect either flux or skin resistivity. Most surfactants with a polar head over the range established for the preferred enhancers of this inventions showed little effect on metoclopramide flux, although some had an effect on skin resistance.

Thus, preferred electrotransport enhancers of the invention are those having a net charge in solution opposite that of the agent, when both the agent and the enhancer are present in ionized form in solution.

Example 2

Measurement of Metoclopramide Flux with Ethanol as Enhancer (Comparison with Prior Art)

The prior art teaches that ethanol can be used to enhance both passive and electrically-assisted transdermal drug delivery. This experiment was run to determine the effects of ethanol (10–30 wt %) on metoclopramide flux and cell voltage under conditions similar to those described in Example 1. The agent utilized, metoclopramide HCl, was placed in the donor compartment at about 100 mg metoclopramide/ml, and Dulbecco's phosphate buffered saline (pH 7) was placed in the receptor compartment. The system was maintained at 32° C. and a constant electric current of 100 µA/cm$^2$ was applied throughout the procedure.

All runs had the same concentration of metoclopramide and other conditions, except for the following shown in Table 2 below.

TABLE 2

Content of Enhancer (Ethanol), Metoclopramide Flux and Cell Voltage

| No. | Type | Enhancer Amount (wt %) | n | Normalized Metoclopramide Mass Flux (after 5 hrs) | Normalized Cell Voltage (after 5 hrs) |
|---|---|---|---|---|---|
| 1 | None | 0 | 1 | 1.00 | 1.00 |
| 2 | Ethanol | 10 | 3 | 0.86 | 0.82 |
| 3 | Ethanol | 20 | 3 | 0.73 | 0.70 |
| 4 | Ethanol | 30 | 3 | 0.93 | 0.78 |

The first line in Table 2 is a control wherein the electrically assisted metoclopramide flux and cell voltage were measured in the absence of ethanol, and each assigned a value of 1.00. The remaining metoclopramide flux and cell voltage values were normalized versus the control. Table 2 shows that the addition of 10 to 30 wt % ethanol to the donor solutions decreased the mass flux of metoclopramide and the skin conductivity.

Example 3

Enhancement of Electrotransport Delivery of Positively Charged Tetracaine

The electrotransport of tetracaine HCl, in the form of an aqueous solution having a concentration of 100 mg/ml, was tested and found to behave similarly to that of metoclopramide HCl. The average mass flux obtained was 100 µg/cm$^2$ hr, and there was a 1 to 2 hour time lag to reach steady state flux.

The electrotransport of tetracaine was also conducted with surfactant flux enhancers, such as decyl methyl sulfoxide. Electrotransport pretreatment with the enhancer was highly beneficial for increasing the mass flux of the agent and decreasing cell voltage.

Tetracaine is a much less electrophilic molecule than metoclopramide since it is positively charged at its tertiary amine group, but the rest of the molecule is very hydrophobic. Concentrations of tetracaine higher than 20 mg/ml (75 mM) lead to the formation of micelles, due to the highly surfactant nature of the drug. Lower concentrations of tetracaine may lead to a better showing of the effect of the enhancer.

Example 4

Di-sodium cromolyn, when in aqueous solution, forms a divalent anion. The experimental conditions were as described in Example 1, except the cromolyn donor solution was placed in the cathodic compartment 46 and the Dulbecco's phosphate buffered saline receptor solution was placed in the anodic compartment 44; and the stratum corneum layer of skin disk 42 was mounted to face the cathodic compartment 46.

Dodecylpyrrolidone, when added to the donor solution, at a concentration of 100 mM, increased cromolyn flux by 50 to 100% and lowered skin resistivity by 30 to 70%.

Example 5

Enhancement of Electrotransport of Ketoprofen

Sodium ketoprofen in aqueous solution forms an univalent anionic anti-inflammatory agent. The electrotransport delivery of 100 mM ketoprofen in the presence of cationic and non-ionic surfactants was tested under the conditions described in Example 1. The enhancers used were laurylamine and dimethyl lauramide. Two sets of tests were conducted. The first in aqueous solution, and the second in 20 wt % ethanol/water solution. Both enhancers utilized increased mass flux and skin conductivity when used in water alone. The addition of 20% ethanol as a solvent improved the performance of both enhancers.

Having thus generally described our invention and certain preferred embodiments thereof, it will be readily apparent to a person of ordinary skill in the art that various modifications to the invention may be made without departing from the scope of this invention, which is limited only by the following claims.

I claim:

1. A composition for the transdermal electrotransport delivery of an agent comprising:

a) at least one agent for transdermal delivery; and b) at least one transdermal electrotransport enhancer having a hydrophile-lipophile balance (HLB) number greater than about 6 and comprising a hydrophobic tail and a polar head of less than about 150 Dalton MW, the polar head group being uncharged or having a charge opposite the charge of the agent to be delivered if the agent is ionizable in solution; wherein the electrotransport enhancer is selected from the group consisting of saturated $C_{10}$–$C_{12}$ aliphatic alcohols, amines, mono- and di-substituted amines, quaternary ammonium salts, sulfoxides, sulfates, amides, mono- and di-substituted amides, esters and salts thereof.

2. The composition of claim 1, wherein the hydrophobic tail of the electrotransport enhancer is a linear $C_{10}$–$C_{12}$ alkyl group.

3. The composition of claim 1, wherein the electrotransport enhancer is selected from the group consisting of lauryl amine, n-decyl methyl sulfoxide, dodecyl pyrrolidone, dimethyl lauramide, sodium lauryl sulfate, salts thereof, and mixtures thereof.

4. The composition of claim 1, wherein the agent and the electrotransport enhancer have charges of opposite sign when in solution.

5. The composition of claim 1, wherein the electrotransport enhancer comprises about 0.01 to 20 wt % of said composition.

6. The composition of claim 1, wherein the electrotransport enhancer is substantially non-ionic in solution.

7. The composition of claim 1, further comprising an additive selected from the group consisting of solvents, solubility enhancers, permeability enhancers, conductivity enhancers, buffers and mixtures thereof.

8. In a transdermal electrotransport device comprising a donor reservoir, a donor electrode electrically connected to the reservoir and an electrical power source electrically connected to the donor electrode, the improvement wherein the donor reservoir comprises the composition of claim 1.

9. A method of electrotransport delivery of an agent through a body surface comprising contacting the body surface with a composition comprising at least one agent to be delivered and at least one transdermal electrotransport enhancer and applying an electrical current therethrough, wherein the enhancer has a hydrophile-lipophile balance (HLB) number greater than about 6, a hydrophobic saturated $C_{10}$–$C_{12}$ aliphatic chain tail and a polar head group of less than about 150 Dalton MW, the polar head group being uncharged or having a charge opposite the charge of the agent to be delivered if the agent is ionizable in solution; the electrotransport enhancer being selected from the group consisting of saturated $C_{10}$–$C_{12}$ aliphatic alcohols, amines, mono and di-substituted amines, quaternary ammonium salts, sulfoxides, sulfates, amides, mono- and di-substituted amides, esters and salts thereof.

10. The method of claim 9, wherein the hydrophobic tail of the electrotransport enhancer is a linear $C_{10}$–$C_{12}$ alkyl group.

11. The method of claim 9, wherein the electrotransport enhancer is selected from the group consisting of lauryl amine, n-decyl methylsulfoxide, dodecyl pyrrolidone, dimethyl lauramide, sodium lauryl sulfate, and mixtures thereof.

12. The method of claim 9, wherein the agent and the electrotransport enhancer have charges of opposite sign in solution.

13. The method of claim 9, wherein the electrotransport enhancer comprises about 0.01 to 20 wt % of said composition.

14. The method of claim 9, wherein the electrotransport enhancer is substantially non-ionic in solution.

15. The method of claim 9, wherein the composition further comprises an additive selected from the group consisting of solvents, solubility enhancers, physical permeability enhancers, conductivity enhancers, buffers and mixtures thereof.

16. A method for delivering an agent by electrotransport through a body surface, comprising contacting the body surface with the device of claim 12; passing an electric current through the composition and the surface; and delivering the agent by electrotransport therethrough.

* * * * *